United States Patent [19]

Turner

[11] 4,147,794

[45] Apr. 3, 1979

[54] TREATMENT OF HYPERTENSION WITH THIADIAZOLES

[75] Inventor: Stephen Turner, Swanland, England

[73] Assignee: Reckitt & Colman Products Limited, London, England

[21] Appl. No.: 804,728

[22] Filed: Jun. 8, 1977

[30] Foreign Application Priority Data

Jun. 17, 1976 [GB] United Kingdom ............... 25079/76

[51] Int. Cl.$^2$ .................... A61K 31/425; C07D 275/00
[52] U.S. Cl. ................................ 424/270; 260/302 D
[58] Field of Search ......................................... 424/270

[56] References Cited

PUBLICATIONS

Shafiee et al., J. of Heter. Chem., Feb. 1976, pp. 117–121.

Primary Examiner—Stanley J. Friedman

Attorney, Agent, or Firm—Bacon & Thomas

[57] ABSTRACT

The invention relates to a method of reducing blood pressure which comprises the oral or parenteral administration of a compound having the formula:

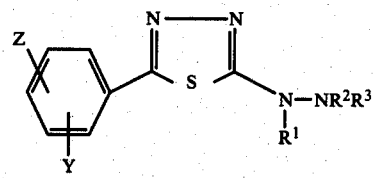

where $R^1$, $R^2$, $R^3$, Z and Y represent specified radicals. The above compounds are administered with a pharmaceutically acceptable diluent or carrier therefor, in the form of a pharmaceutical composition.

12 Claims, No Drawings

TREATMENT OF HYPERTENSION WITH THIADIAZOLES

This invention relates to therapeutic compositions and in particular to therapeutic compositions which may be used in the treatment of disorders of the cardiovascular system.

According to this invention there are provided therapeutic compositions comprising a compound of the formula:

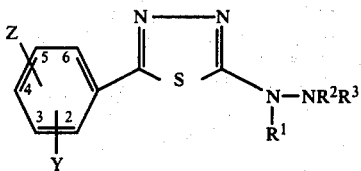

wherein
$R^1$ is hydrogen or methyl;
$R^2$ is hydrogen, alkyl $C_{1-4}$, or acetyl;
$R^3$ is hydrogen or alkyl $C_{1-4}$;
Z is hydrogen, methyl, methoxy, fluoro or chloro;
Y is alkyl $C_{1-7}$, alkoxy $C_{1-6}$, fluoro, chloro, bromo, iodo, alkylsulphinyl $C_{1-4}$, trifluoromethyl, methylthio, nitro, phenyl or substituted phenyl, at the 2-position; or when Z is hydrogen, Y may be hydrogen or may be chloro, methyl or hydroxy at the 3-or 4-positions; or a pharmaceutically acceptable acid addition salt thereof; and a pharmaceutically acceptable diluent or carrier.

In a modification of the invention when in the compounds of Formula I both Y and Z are methoxy in the 2- and 6- positions there may be a chloro substituent in the 3-position.

Preferred compositions are those containing as active ingredient a compound of Formula I wherein
$R^1$ is hydrogen or methyl;
$R^2$ is hydrogen or methyl;
$R^3$ is hydrogen or methyl;
Y is hydrogen, alkyl $C_{1-4}$, alkoxy $C_{1-3}$, fluoro, bromo, iodo, alkylsulphinyl $C_{1-4}$, trifluoromethyl, or methylthio at the 2-position;
Z is hydrogen; or a pharmaceutically acceptable acid addition salt thereof.

Particularly preferred compositions are those containing as active ingredient a compound of Formula I wherein $R^1$, $R^2$ and $R^3$ are hydrogen, Y is bromo, iodo or methyl at the 2-position, and Z is hydrogen.

Other particularly preferred compositions are those containing as active ingredient a compound of Formula I in which $R^1$, $R^2$, $R^3$ and Z are hydrogen and Y is trifluoromethyl or methylsulphinyl at the 2-position or a pharmaceutically acceptable acid addition salt thereof.

Other preferred compositions are those containing as active ingredient a compound of Formula I which is 2-hydrazino-5-(2-ethylphenyl)-1,3,4-thiadiazole; 2-hydrazino-5-(2-tert-butylphenyl)-1,3,4-thiadiazole; 2-(2-acetylhydrazino)-5-(2-methylphenyl)-1,3,4-thiadiazole; 2-hydrazino-5-(2-n-propoxyphenyl)-1,3,4-thiadiazole; 2-hydrazino-5-(2-n-propylsulphinylphenyl)-1,3,4-thiadiazole; 2-hydrazino-5-(2,3-dimethylphenyl)-1,3,4-thiadiazole; 2-hydrazino-5-(2,4-dimethylphenyl)-1,3,4-thiadiazole; 2-hydrazino-5-(2,5-dimethylphenyl)-1,3,4-thiadiazole; 2-hydrazino-5-(2,6-dimethylphenyl)-1,3,4-thiadiazole; 2-hydrazino-5-(2,6-dimethoxyphenyl)-1,3,4-thiadiazole; 2-hydrazino-5-(2,6-dimethoxy-3-chlorophenyl)-1,3,4-thiadiazole; 2-hydrazino-5-(2,6-dichlorophenyl)-1,3,4-thiadiazole; or 2-hydrazino-5-(2-methyl-4-fluorophenyl)-1,3,4-thiadiazole; or a pharmaceutically acceptable acid addition salt thereof.

The compositions produce a significant reduction in blood pressure when administered to rats rendered hypertensive and may therefore be useful in the treatment of those conditions in man for which an anti-hypertensive or vasodilator drug is employed.

Some of the compounds of Formula I are known compounds, however pharmacological activity had not previously been reported for such compounds. The known compounds include those in which Y is hydrogen, methyl or chloro when $R^1$, $R^2$, $R^3$ and Z are hydrogen; Y, Z, $R^2$ and $R^3$ are hydrogen when $R^1$ is methyl.

Some of the compounds of Formula I in which Y is alkyl-sulphinyl, $C_{1-4}$ or methylthio at the 2-position are novel compounds. It is to be understood that these compounds form part of the present invention, when $R^1$, $R^2$, $R^3$ and Z are as hereinbefore defined.

The compounds of Formula I in which $R^1$, $R^2$ and $R^3$ are hydrogen may be prepared from the compounds of Formula II,

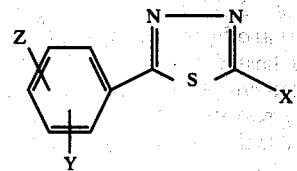

in which Y and Z are as hereinbefore defined and X is chloro or bromo by reaction with hydrazine hydrate.

Those compounds of Formula I in which $R^1$ is methyl may be prepared by analogous techniques utilizing methyl hydrazine or by methods well known to those skilled in the art.

Those compounds of Formula I in which $R^2$ is acetyl may be prepared from the analogous compounds in which $R^2$ is hydrogen, by treatment with acetyl chloride or acetic anhydride, preferably in the presence of a base such as pyridine.

Those compounds of Formula I in which $R^2$ is alkyl $C_{1-4}$ may be prepared from the analogous compounds in which $R^2$ is acyl by forming a metal salt (such as the sodium salt by treatment with sodium ethoxide), alkylating this using for example an alkyl halide, followed by hydrolysis. The alkyl compounds may also be prepared by reduction of an acyl compound using for example lithium aluminium hydride.

Compounds of Formula I in which $R^1$, $R^2$ and/or $R^3$ are other than hydrogen may be prepared by combinations of the above described processes, or by processes well known to those skilled in the art.

The therapeutic compositions may be in a form suitable for oral or parenteral administration. Such oral compositions may be in the form of capsules, tablets, granules or liquid preparations such as elixirs, syrups or suspensions.

Tablets contain a compound of Formula I in admixture with excipients which are suitable for the manufacture of tablets. These excipients may be inert diluents such as calcium phosphate, microcrystalline cellulose, lactose, sucrose or dextrose; granulating and disintegrating agents such as starch; binding agents such as starch, gelatine, polyvinylpyrrolidone or gum acacia; and lubricating agents such as magnesium stearate, stearic acid or talc.

Compositions in the form of capsules may contain a compound of Formula I mixed with an inert solid diluent such as calcium phosphate, lactose or Kaolin in a hard gelatine capsule.

Compositions for parenteral administration may be in the form of sterile injectable preparations containing a compound of Formula I as active ingredient. Such preparations may be solutions or suspensions in, for example, water, saline, dextrose or 1,3-butane diol.

For the purposes of convenience and accuracy of dosing the compositions are advantagesouly employed in a unit dosage form. For oral administration the unit dosage form contains from 1 to 500 mg, preferably 25 to 300 mg of the compound of Formula I. Parenteral unit dosage forms contain from 1 to 30 mg of the compound of Formula I per 1 ml of the preparation.

The following examples illustrate the preparation of compounds which may be used in the preparation of the therapeutic compositions of the invention:

EXAMPLE 1

2-Hydrazino-5-(2-methylphenyl)-1,3,4-thiadiazole

A mixture of 2-chloro-5-(2-methylphenyl)-1,3,4-thiadiazole (3.0 g) and hydrazine hydrate (3ml) in ethanol (80 ml) was heated under reflux for 2 hr. After removal of the solvent, water was added and the mixture filtered. The residue was dissolved in hot 2N hydrochloric acid (20 ml), cooled, filtered and crystallised from methanol-ether to give the desired product as the hydrochloride (1.62 g; 47%), m.p. 169°–72°, $C_9H_{10}N_4S.HCl$ requires C, 44.5; H, 4.5; N, 23.1; S, 13.2: Found C, 44.5; H, 4.7; N, 23.2; S, 13.1%

EXAMPLE 2

2-(2-Acetylhydrazino)-5-(2-methylphenyl)-1,3,4-thiadiazole

A solution of 2-hydrazino-5-(2-methylphenyl)-1,3,4-thiadiazole hydrochloride (1.0 g) in a mixture of acetic anhydride (0.5 ml) and pyridine (0.5 ml) was kept at room temperature under nitrogen for 0.5 hr. The solution was poured into water (100 ml) and extracted three times with methylene chloride. The organic layer was evaporated and the residue was fractionated on two 20 × 20 cm, 2 mm thick silica preparative t.l.c. plates by eluting with chloroform-methanol (4:1). The resultant product was crystallised from ethyl acetate (0.32 g; 31%) m.p. 165°–6°. $C_{11}H_{12}N_4OS$ requires C, 52.8; H, 5.6; N, 22.4; S, 12.8 Found C, 52.8; H, 5.1; N, 22.8; S, 13.2%

EXAMPLE 3

2-(2-methylhydrazino)-5-(2-methylphenyl)-1,3,4-thiadiazole (a) 2-(2-Acetylhydrazino)-5-(2-methylphenyl)-1,3,4-thiadiazole (6.30 g) was added to a stirred solution of sodium (0.57 g) in ethanol (63 ml) at room temperature. After 15 minutes methyl iodide (7.10 g) was added and the solution kept at room temperature for 3½ hours. The solvent was removed in vacuo and the residue chromatographed on a silica column (315 g) using mixtures of methanol and chloroform, finally eluting with 5% methanolchloroform. The resultant product was crystallised from ethyl acetate to give 2-(2-acetyl-2-methylhydrazino)-5-(2-methylphenyl)-1,3,4-thiadiazole (4.57 g) m.p. 106°–8°.

(b) The above acetyl derivative (3.50 g), was hydrolysed by heating under reflux in 50% hydrochloric acid (20 ml) for 4 hours. The solution was cooled, filtered and the product crystallised from ethanol-ether to give 2-(2-methylhydrazino)-5-(2-methylphenyl)-1,3,4-thiadiazole (2.12 g) as its hydrochloride m.p. 202°–4°.

TABLE

| Example | Subst. in benzene ring | | | | | Yield | m.p. | Calculated / % Found | | | | Formula |
| | 2 | 3 | 4 | 5 | 6 | | | C | H | N | S | |
|---|---|---|---|---|---|---|---|---|---|---|---|---|
| 4 | Cl | | | | | 39% | 174–6 | 36.5 / 36.5 | 3.1 / 3.0 | 21.3 / 21.0 | 12.2 / 12.1 | $C_8H_7ClN_4S \cdot HCl$ |
| 5 | Br | | | | | 69% | 158–61 | 31.2 / 31.3 | 2.6 / 2.6 | 18.2 / 18.2 | 10.4 / 10.6 | $C_8H_7BrN_4S \cdot HCl$ |
| 6 | I | | | | | 40% | 157–9 | 27.1 / 27.3 | 2.3 / 2.3 | 15.8 / 15.8 | 9.0 / 8.7 | $C_8H_7IN_4S \cdot HCl$ |
| 7 | MeO | | | | | 56% | 177–80 | 41.8 / 42.0 | 4.2 / 4.2 | 21.7 / 22.3 | 12.4 / 12.4 | $C_9H_{10}N_4OS \cdot HCl$ |
| 8 | MeSO | | | | | 64% | 190–2 | 37.2 / 36.9 | 3.8 / 4.0 | 19.3 / 19.5 | 22.0 / 21.8 | $C_9H_{10}N_4OS_2 \cdot HCl$ |
| 9 | F | | | | | 52% | 231–2 | | | | | $C_8H_7FN_4S \cdot HCl$ |
| 10 | CF_3 | | | | | 15% | 179–81 | 36.4 / 36.3 | 2.7 / 2.8 | 18.9 / 18.7 | 10.8 / 11.0 | $C_9H_7F_3N_4S \cdot HCl$ |
| 11 | unsubstituted | | | | | 59% | 201–3 | | | | | $C_8H_8N_4S \cdot HCl$ |
| 12 | " | | | | | 30% | 183–5 | | | | | $C_{10}H_{10}N_4OS$ |
| 13 | " | | | | | 43% | 148–9 | | | | | $C_9H_{10}N_4S$ |
| 14 | " | | | | | 50% | 195–9 | 44.5 / 44.6 | 4.6 / 4.7 | 23.1 / 23.2 | 13.2 / 13.2 | $C_9H_{10}N_4S \cdot HCl$ |
| 15 | Cl | | | Cl | | 56% | 185–7 | 36.8 / 37.1 | 2.3 / 2.2 | 21.5 / 21.8 | 12.3 / 12.2 | $C_8H_6Cl_2N_4S$ |
| 16 | MeO | Cl | | MeO | | 21% | 113–5 | 37.1 / 36.9 | 4.0 / 4.1 | 17.3 / 17.3 | 9.9 / 10.0 | $C_{10}H_{11}ClN_4O_2S \cdot HCl$ |
| 17 | | Cl | | | | 51% | 172(d) | | | | | $C_8H_7ClN_4S \cdot HCl$ |
| 18 | | Me | | | | 62% | 152–5 | 44.5 / 44.4 | 4.6 / 4.6 | 23.1 / 23.0 | 13.2 / 13.4 | $C_9H_{10}N_4S \cdot HCl$ |
| 19 | | | Cl | | | 28% | 185–90 | | | | | $C_8H_7ClN_4S \cdot HCl$ |
| 20 | NO_2 | | | | | 41% | 166–72 | 35.1 / 35.3 | 2.9 / 2.9 | 25.6 / 25.5 | 11.7 / 11.9 | $C_8H_7N_5SO_2 \cdot HCl$ |
| 21 | MeO | | | MeO | | 38% | 188–91 | 41.6 | 4.5 | 19.4 | 11.1 | $C_{10}H_{12}N_4O_2S \cdot HCl$ |

TABLE-continued

| Example | Subst. in benzene ring | | | | | Yield | m.p. | Calculated % Found | | | | Formula |
|---|---|---|---|---|---|---|---|---|---|---|---|---|
| | 2 | 3 | 4 | 5 | 6 | | | C | H | N | S | |
| 22 | | | Me | | | 32% | 176–80 | 41.7 | 4.7 | 19.6 | 11.1 | $C_9H_{10}N_4S \cdot HCl$ |
| 23 | Me | | | Me | | 31% | 171–4 | 46.8 | 5.1 | 21.8 | 12.5 | $C_{10}H_{12}N_4S \cdot HCl$ |
| | | | | | | | | 46.5 | 5.3 | 22.0 | 12.9 | |
| 24 | Et | | | | | 37% | 135–8 | 46.8 | 5.1 | 21.8 | 12.5 | $C_{10}H_{12}N_4S \cdot HCl$ |
| | | | | | | | | 46.9 | 5.0 | 21.6 | 12.6 | |
| 25 | Me | Me | | | | 54% | 161–4 | 46.8 | 5.1 | 21.8 | 12.5 | $C_{10}H_{12}N_4S \cdot HCl$ |
| | | | | | | | | 47.3 | 5.3 | 21.9 | 12.3 | |
| 26 | Me | | | Me | | 22% | 196–9 | 46.8 | 5.1 | 21.8 | 12.5 | $C_{10}H_{12}N_4S \cdot HCl$ |
| 27 | SMe | | | | | 39% | 160–2 | 39.6 | 4.0 | 20.6 | 23.5 | $C_9H_{10}N_4S_2 \cdot HCl$ |
| | | | | | | | | 39.7 | 4.2 | 20.3 | 23.1 | |
| 28 | Me | | Me | | | 21% | 146–50 | 43.7 | 5.5 | 20.4 | 11.7 | $C_{10}H_{12}N_4S \cdot HCl \cdot H_2O$ |
| | | | | | | | | 43.3 | 5.7 | 20.9 | 12.4 | |
| 29 | Me | | F | | | 48% | 175–9 | 41.5 | 4.0 | 21.5 | 12.5 | $C_9H_9FN_4S \cdot HCl$ |
| | | | | | | | | 41.4 | 3.9 | 21.3 | 12.5 | |
| 30 | $SOPr^n$ | | | | | 45% | 163–6 | 41.4 | 4.7 | 17.6 | 20.1 | $C_{11}H_{14}N_4OS_2 \cdot HCl$ |
| | | | | | | | | 41.2 | 4.9 | 17.6 | 19.8 | |
| 31 | $OPr^n$ | | | | | 25% | 146–50 | 46.1 | 5.3 | 19.5 | 11.2 | $C_{11}H_{14}N_4OS \cdot HCl$ |
| 32 | $Bu^t$ | | | | | 16% (free base) | 155–7 | 58.0 | 6.5 | 22.6 | 12.9 | $C_{12}H_{16}N_4S$ |
| 33 | | | Me | | | 51 | 168–170 | 46.8 | 5.1 | 21.8 | 12.5 | $C_{10}H_{12}N_4S \cdot HCl$ |
| | | | | | | | | 46.9 | 5.2 | 22.3 | 12.0 | |

The Table sets out details of further examples of compounds of Formula I in which $R^1$, $R^2$ and $R^3$ are hydrogen except that in Example 12 $R^2$ is acetyl, in Example 13 $R^1$ is methyl and Example 14 $R^2$ is methyl, in Example 33 $R^1$ is methyl. The compound of Example 12 was prepared by the method of Example 2, compound of Example 14 by the method of Example 3 (yield quoted is for the final stage) the remaining Examples being prepared by the method of Example 1. Screening for anti-hypertensive activity has been carried out using DOCA hypertensive rats according to the method of Stanton H. C. and White J. B., Arch. Int. Pharmacodyn. Ther. 154, No. 2 351 (1966) and Weeks J. R. and Jones J. A., Proc. Exper. Biol. & Med. 104, No. 4, 646 (1960).

In this test when compounds were administered orally at a dose of 100 mg/Kg to groups of DOCA hypertensive rats the maximum percentage fall in the mean arterial blood pressure were:

| No. of Example | % Fall in blood pressure |
|---|---|
| 1 | 63 |
| 2 | 41 |
| 5 | 48 |
| 6 | 52 |
| 7 | 45 |
| 8 | 55 |
| 9 | 31 |
| 10 | 50 |
| 11 | 42 |
| 13 | 37 i.p. |
| 15 | 50 |
| 16 | 53 |
| 23 | 50 |

Additionally, some of the compounds of the invention exhibit anticonvulsant or antidepressant activity. Screening for anticonvulsant activity has been carried out employing known pharmacological tests such as Strychnine antagonism in mice (J. Pharm. exp. Therap., 132, 360 (1962)), and Leptazol antagonism in mice (Ibid., 138, 224 (1962)) and Electroshock seizures in mice (Ibid., 106, 319 (1952)). Screening for antidepressant activity has been carried out using the Picrotoxin test (Brit. J. Pharmacol. 52, 432P (1974)). Indications are that antihypertensive activity tends to fall as the bulk of groups $R^2$ and $R^3$ increases whilst the level of anticonvulsant activity tends to increase.

The compound of Example 4 when administered intraperitoneally in the laptazol test had an $ED_{50}$ of 47 mg/Kg and in the electroshock test the $ED_{50}$ was 50 mg/Kg. The compound of Example 7 when administered intraperitoneally had an $ED_{50}$ of 1.9 mg/Kg in the picrotoxin test. With the compound of Example 17 when administered intraperitoneally $ED_{50}'$ were: strychnine test 54.6 mg/Kg, leptazol test 62.0 mg/kg and picrotoxin test 3.1 mg/Kg.

The invention is further illustrated by the following Examples of compositions in which all parts are by weight.

EXAMPLE I

A mixture of 1 part of 2-hydrazino-5-(2-bromophenyl)-1,3,4-thiadiazole hydrochloride and 3 parts of microcrystalline cellulose together with 1% of magnesium stearate is compressed into tablets. Conveniently the tablets are of such a size as to contain 25 mg of the active ingredient. Similar tablets containing 50 mg of the active ingredient may be prepared from a mixture of equal parts of active ingredient and microcrystalline cellulose together with 1% of magnesium stearate.

EXAMPLE II

A mixture of 1 part of 2-hydrazino-5-(2-bromophenyl)-1,3,4-thiadiazole hydrochloride and 3 parts of spray dried lactose together with 1% of magnesium stearate is filled into hard gelatine capsules. The capsules may conveniently contain 25 mg of the active ingredient. Similar capsules containing 50 mg of the active ingredient may be prepared from a mixture of equal parts of active ingredient and spray dried lactose together with 1% of magnesium stearate.

EXAMPLE III

The active ingredient in each of Examples I to II may be replaced by 2-hydrazino-5-(2-methylphenyl)-1,3,4-thiadiazole hydrochloride, 2-hydrazino-5-(2-iodophenyl)-1,3,4-thiadiazole hydrochloride, 2-hydrazino-5-

(2-trifluoromethylphenyl)-1,3,4-thiadiazole hydrochloride or 2-hydrazino-5-(2-methylsulphinylphenyl)-1,3,4-thiadiazole hydrochloride.

EXAMPLE IV

The active ingredients in each of Examples I to II may be replaced by 2-hydrazino-5-(2-ethylphenyl)-1,3,4-thiadiazole hydrochloride, 2-hydrazino-5-(2-tert-butylphenyl)-1,3,4-thiadiazole hydrochloride, 2-(2-acetylhydrazino)-5-(2-methylphenyl)-1,3,4-thiadiazole hydrochloride, 2-hydrazino-5-(2-n-propoxyphenyl)-1,3,4 thiadiazole hydrochloride, 2-hydrazino-5-(2,3-dimethylphenyl)-1,3,4 thiadiazole hydrochloride, 2-hydrazino-5-(2,3-dimethylphenyl)-1,3,4-thiadiazole hydrochloride, 2-hydrazino-5-(2,4-dimethylphenyl)-1,3,4-thiadiazole hydrochloride, 2-hydrazino-5-(2,5-dimethylphenyl)-1,3,4-thiadiazole hydrochloride, 2-hydrazino-5-(2,6-dimethylphenyl)-1,3,4-thiadiazole hydrochloride, 2-hydrazino-5-(2,6-dimethoxy-3-chlorophenyl)-1,3,4-thiadiazole hydrochloride, 2-hydrazino-5-(2,6-dichlorophenyl)-1,3,4-thiadiazole hydrochloride or 2-hydrazino-5-(2,6-dimethyloxyphenyl)-1,3,4-thiadiazole hydrochloride.

I claim :

1. A method for treating hypertension which comprises administering to humans an antihypertensive effective amount of a compound of the formula

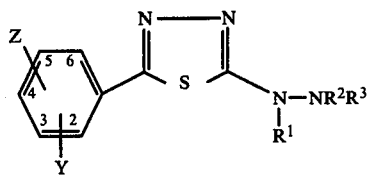

wherein
$R^1$ is hydrogen or methyl;
$R^2$ is hydrogen, alkyl $C_{1-4}$ or acetyl;
$R^3$ is hydrogen or alkyl $C_{1-4}$;
Z is hydrogen, methyl, methoxy, fluoro, or chloro;
Y is alkyl $C_{1-7}$, alkoxy $C_{1-6}$, fluoro, chloro, bromo, iodo, alkylsulphinyl $C_{1-4}$, trifluoromethyl, methylthio, nitro, phenyl or substituted phenyl at the 2-position; or when Z is hydrogen, Y may be hydrogen or may be chloro, methyl or hydroxy at the 3- or 4-positions; or a pharmaceutically acceptable acid addition salt thereof.

2. A method for treating hypertension which comprises administering to humans an antihypertensive effective amount of a compound of the formula

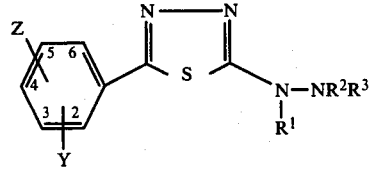

wherein
$R^1$ is hydrogen or methyl;
$R^2$ is hydrogen, alkyl $C_{1-4}$ or acetyl;
$R^3$ is hydrogen or alkyl $C_{1-4}$;
Z is hydrogen, methyl, methoxy, fluoro or chloro;
Y is alkyl $C_{1-4}$, alkoxy $C_{1-3}$, fluoro, chloro, bromo, iodo, alkylsulphinyl $C_{1-4}$, trifluoromethyl, methylthio, nitro, phenyl or substituted phenyl at the 2-position; or when Z is hydrogen, Y may be hydrogen or may be chloro, methyl or hydroxy at the 3- or 4-positions; or a pharmaceutically acceptable acid addition salt thereof.

3. A method of treatment as claimed in claim 2 in which in the compound of Formula I, $R^1$ is hydrogen or methyl; $R^2$ is hydrogen or methyl; $R^3$ is hydrogen or methyl; Y is hydrogen, alkyl $C_{1-4}$, alkoxy $C_{1-3}$, fluoro, bromo, iodo, alkylsulphinyl $C_{1-4}$, trifluoromethyl or methylthio at the 2-position; Z is hydrogen; or a pharmaceutically acceptable addition salt thereof.

4. A method of treatment as claimed in claim 2 in which in the compound of Formula I, $R^1$, $R^2$ and $R^3$ are hydrogen, Y is bromo, iodo or methyl at the 2-position; Z is hydrogen; or a pharmaceutically acceptable addition salt thereof.

5. A method of treatment as claimed in claim 2 in which in the compound of Formula I, $R^1$, $R^2$, $R^3$ and Z are hydrogen and Y is trifluoromethyl or methylsulphinyl at the 2-position; or a pharmaceutically acceptable acid addition salt thereof.

6. A method of treatment as claimed in claim 1 in which the compound is 2-hydrazino-5-(2-ethylphenyl)-1,3,4-thiodiazole; 2-hydrazino-5-(2-tert-butylphenyl)-1,3,4-thiadiazole; 2-(2-acetylhydrazino)-5-(2-methylphenyl)-1,3,4-thiadiazole; 2-hydrazino-5-(2,6-dimethoxyphenyl)-1,3,4-thiadiazole; 2-hydrazino-5-(2-n-propylsulphenyl)-1,3,4-thiadiazole; 2-hydrazino-5-(2-n-propylsulphinylphenyl)-1,3,4-thiadiazole; 2-hydrazino-5-(2,4-dimethylphenyl)-1,3,4-thiadiazole; 2-hydrazino-5-(2,4-dimethylphenyl)-1,3,4-thiadiazole; 2-hydrazino-5-(2,5-dimethylphenyl)-1,3,4-thiadiazole; 2-hydrazino-5-(2,6-dimethylphenyl)-1,3,4-thiadiazole; 2-hydrazino-5-(2,6-dimethoxy-3-chlorophenyl)-1,3,4-thiadiazole; 2-hydrazino-5-(2,6-dichlorophenyl)-1,3,4-thiadiazole or 2-hydrazino-5-(2-methyl-4-fluorophenyl)-1,3,4-thiadiazole or a pharmaceutically acceptable acid addition salt thereof.

7. A composition in unit dosage form for oral administration for the treatment of hypertension which comprises an antihypertensive effect amount of from 25 to 300 mg of a compound of the formula:

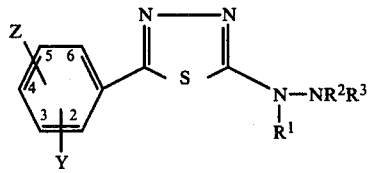

wherein
$R^1$ is hydrogen or methyl;
$R^2$ is hydrogen, alkyl $C_{1-4}$ or acetyl;
$R^3$ is hydrogen or alkyl $C_{1-4}$;
Z is hydrogen, methyl, methoxy, fluoro, or chloro;
Y is alkyl $C_{1-7}$, alkoxy $C_{1-6}$, fluoro, chloro, bromo, iodo-, alkylsulphinyl $C_{1-4}$, trifluoromethyl, methylthio, nitro, phenyl or substituted phenyl at the 2-position; or when
Z is hydrogen, Y may be hydrogen or may be chloro, methyl or hydroxy at the 3- or 4-position; or a pharmaceutically acceptable acid addition salt thereof; and a pharmaceutically acceptable solid diluent or carrier.

8. A therapeutic composition in unit dosage form for oral administration for the treatment of hypertension which comprises an antihypertensive effective amount of from 25 to 300 mg of a compound of formula:

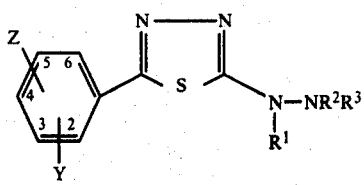

wherein
- $R^1$ is hydrogen or methyl;
- $R^2$ is hydrogen, alkyl $C_{1-4}$ or acetyl;
- $R^3$ is hydrogen or alkyl $C_{1-4}$;
- Z is hydrogen, methyl, methoxy, fluoro, or chloro;
- Y is alkyl $C_{1-4}$, alkoxy $C_{1-3}$, fluoro, chloro, bromo, iodo, alkylsulphinyl $C_{1-4}$, trifluoromethyl, methylthio, nitro, phenyl or substituted phenyl at the 2-position; or when Z is hydrogen, Y may be hydrogen or may be chloro, methyl or hydroxy at the 3- or 4-positions; or a pharmaceutically acceptable acid addition salt thereof; and a pharmaceutically acceptable solid diluent or carrier.

9. A therapeutic composition as claimed in claim 8 in which in the compound of Formula I, $R^1$ is hydrogen or methyl; $R^2$ is hydrogen or methyl; $R^3$ is hydrogen or methyl; Y is hydrogen, alkyl $C_{1-4}$, alkoxy $C_{1-3}$, fluoro, bromo, iodo, alkylsulphinyl $C_{1-4}$, trifluoromethyl or methylthio at the 2-position; Z is hydrogen; or a pharmaceutically acceptable addition salt thereof.

10. A therapeutic composition as claimed in claim 8 in which in the compound of Formula I, $R^1$, $R^2$ and $R^3$ are hydrogen, Y is bromo, iodo or methyl at the 2-position; Z is hydrogen; or a pharmaceutically acceptable addition salt thereof.

11. A therapeutic composition as claimed in claim 8 in which the compound of Formula I, $R^1$, $R^2$, $R^3$ and Z are hydrogen and Y is trifluoromethyl or methylsulphinyl at the 2-position; or a pharmaceutically acceptable acid addition salt thereof.

12. A therapeutic composition as claimed in claim 7 in which the compound is 2-hydrazino-5-(2-ethylphenyl)-1,3,4-thiadiazole; 2-hydrazino-5-(2-tert-butylphenyl)-1,3,4-thiadiazole; 2-hydrazino-5-(2,6-dimethoxyphenyl)-1,3,4-thiadiazole; 2-(2-acetylhydrazino)-5-(2-methylphenyl)-1,3,4-thiadiazole; 2-hydrazino-5-(2-n-propoxyphenyl)-1,3,4-thiadiazole; 2-hydrazino-5-(2-n-propylsulphinylphenyl)-1,3,4-thiadiazole; 2-hydrazino-5-(2,3-dimethylphenyl)-1,3,4-thiadiazole; 2-hydrazino-5-(2,4-dimethylphenyl)-1,3,4-thiadiazole; 2-hydrazino-5-(2,5-dimethylphenyl)-1,3,4-thiadiazole; 2-hydrazino-5-(2,6-dimethylphenyl)-1,3,4-thiadiazole; 2-hydrazino-5-(2,6-dimethoxy-3-chlorophenyl)-1,3,4-thiadiazole; 2-hydrazino-5-(2,6-dichlorophenyl)-1,3,4-thiadiazole; 2-hydrazino-5-(2,6-dichlorophenyl)-1,3,4-thiadiazole or 2-hydrazino-5-(2-methyl-4-fluorophenyl)-1,3,4-thiadiazole or a pharmaceutically acceptable acid addition salt thereof.

* * * * *

UNITED STATES PATENT AND TRADEMARK OFFICE
CERTIFICATE OF CORRECTION

PATENT NO. : 4,147,794
DATED : April 3, 1979
INVENTOR(S) : Stephen TURNER

It is certified that error appears in the above—identified patent and that said Letters Patent are hereby corrected as shown below:

Column 8, lines 26 and 27, the compound "2-hydrazino-5-(2-n-propyl-sulphenyl)-1,3,4-thiadiazole" should be cancelled;

line 28, please cancel "(2,4-" and insert instead "(2,3-".

Column 10, lines 24 and 25, cancel "2-hydrazino-5-(2,6-dichlorophenyl)-1,3,4-thiadiazole".

Signed and Sealed this

Seventh Day of August 1979

[SEAL]

Attest:

LUTRELLE F. PARKER
Attesting Officer     Acting Commissioner of Patents and Trademarks